United States Patent [19]

Lau et al.

[11] Patent Number: 5,149,703
[45] Date of Patent: Sep. 22, 1992

[54] QUINOLINE-SUBSTITUTED CHROMANS AND RELATED COMPOUNDS AS LEUKOTRIENE ANTAGONISTS

[75] Inventors: Cheuk K. Lau, Ile Bizard; Claude Dufresne, Dollard des Ormeaux, both of Canada

[73] Assignee: Merck Frosst Canada, Inc., Kirland, Canada

[21] Appl. No.: 755,906

[22] Filed: Sep. 6, 1991

[51] Int. Cl.$^5$ ............ A61K 31/47; C07D 405/12; C07D 409/12; C07D 215/14
[52] U.S. Cl. .................. 514/311; 514/314; 544/49; 546/172; 546/174; 546/175; 546/176; 546/180
[58] Field of Search ........... 546/172, 174, 175, 176, 546/180; 514/311, 314

[56] References Cited

U.S. PATENT DOCUMENTS

| | | | |
|---|---|---|---|
| 4,876,346 | 10/1989 | Musser et al. | 546/174 |
| 5,015,661 | 5/1991 | Armin | 514/443 |
| 5,082,849 | 1/1992 | Huang et al. | 546/174 |

FOREIGN PATENT DOCUMENTS

| | | |
|---|---|---|
| 0313295 | 4/1989 | European Pat. Off. . |
| 0313296 | 4/1989 | European Pat. Off. . |
| 0318093 | 5/1989 | European Pat. Off. . |
| 0349062 | 1/1990 | European Pat. Off. . |
| 0391624 | 10/1990 | European Pat. Off. . |
| 0391625 | 10/1990 | European Pat. Off. . |
| 0399818 | 11/1990 | European Pat. Off. . |

Primary Examiner—Alan L. Rotman
Assistant Examiner—James H. Turnipseed
Attorney, Agent, or Firm—Gabriel Lopez; Joseph F. DiPrima

[57] ABSTRACT

Compounds having the formula I:

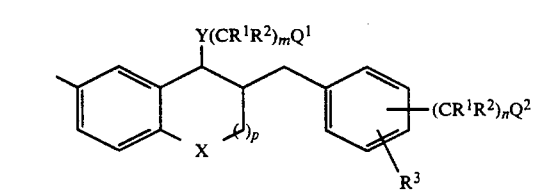

are antagonists of the actions of leukotrienes. These compounds are useful as anti-asthmatic, anti-allergic, anti-inflammatory, and cytoprotective agents. They are also useful in treating angina, cerebral spasm, glomerular nephritis, hepatitis, endotoxemia, uveitis, and allograft rejection.

4 Claims, No Drawings

QUINOLINE-SUBSTITUTED CHROMANS AND RELATED COMPOUNDS AS LEUKOTRIENE ANTAGONISTS

BACKGROUND

The leukotrienes constitute a group of locally acting hormones, produced in living systems from arachidonic acid. The major leukotrienes are Leukotriene $B_4$ (abbreviated at $LTB_4$), $LTC_4$, $LTD_4$, and $LTE_4$. The biosynthesis of these leukotrienes begins with the action of the enzyme 5-lipoxygenase on arachidonic acid to produce the epoxide known as Leukotriene $A_4$ ($LTA_4$), which is converted to the other leukotrienes by subsequent enzymatic steps. Further details of the biosynthesis as well as the metabolism of the leukotrienes are to be found in the book *Leukotrienes and Lipoxygenases*, ed. J. Rokach, Elsevier, Amsterdam (1989). The actions of the leukotrienes in living systems and their contribution to various diseases states are also discussed in the book by Rokach.

European patent applications 318,093 (May 31, 1989), 349,062 (Jan. 3, 1990), and 399,818 (Nov. 28, 1990), disclose structures of leukotriene antagonists and inhibitors of leukotriene biosynthesis which differ from the present compounds in not having chromans, tetralins, or indanes present in them. European patent applications 313,295 (Apr. 26, 1989), 313,296 (Apr. 26, 1989), 391,624 (Oct. 10, 1990), and 391,625 (Oct. 10, 1990) describe quinoline-containing leukotriene biosynthesis inhibitors and/or antagonists which differ from the present compound most notably in that the chroman, thiochroman, tetraline, or indane moiety contains only one acidic side chain and a secondary alcohol. The structures of the compounds disclosed in the above patent applications are shown below.

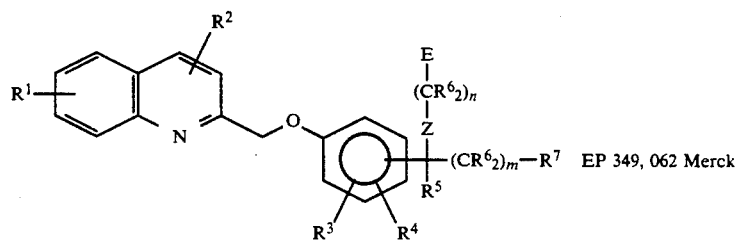

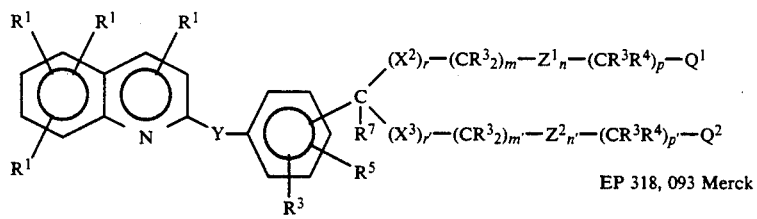

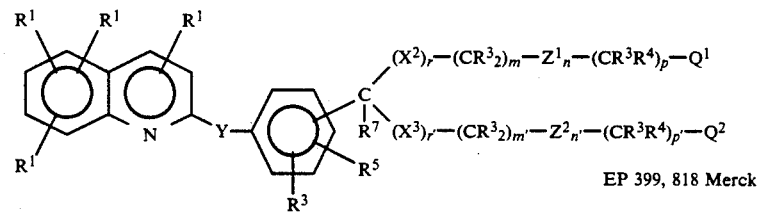

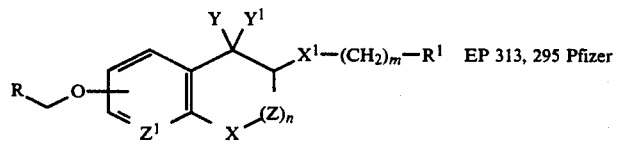

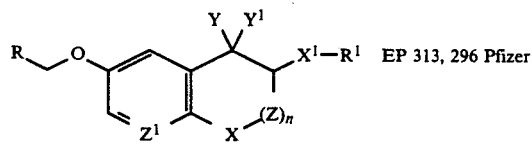

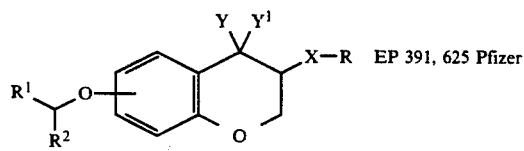

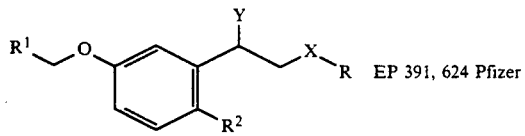
EP 391, 624 Pfizer

SUMMARY OF THE INVENTION

The present invention relates to quinoline-substituted chromans and related compounds having activity as leukotriene antagonists, to methods for their preparation, and to methods and pharmaceutical formulations for using these compounds in mammals (especially humans).

Because of their activity as leukotriene antagonists, the compounds of the present invention are useful as anti-asthmatic, anti-allergic, anti-inflammatory and cytoprotective agents. They are also useful in treating angina, cerebral spasm, glomerular nephritis, hepatitis, endotoxemia, uveitis, and allograft rejection.

DETAILED DESCRIPTION OF THE INVENTION

The compounds of the present invention are represented by Formula I:

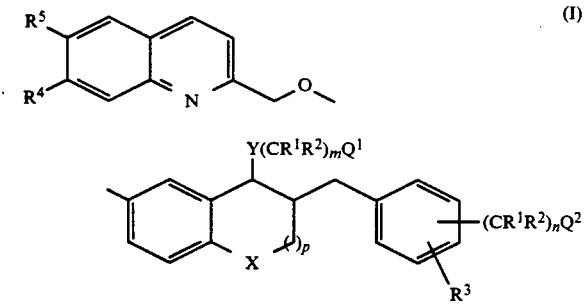

wherein:
each of $R^1$ and $R^2$ is independently H or lower alkyl;
$R^3$ is H or Cl
$R^4$ is Cl or Br;
$R^5$ is H, Cl or Br; each of $R^6$ and $R^7$ is independently H or lower alkyl;
$R^8$ is alkyl, substituted or unsubstituted phenyl, or $CF_3$;
$R^9$ is H, lower alkyl, or $CF_3$;
Each of $Q^1$ and $Q^2$ is independently $CO_2H$, $CONR^1R^2$, 1H-(or 2H-)tetrazol-5-yl, $COR^9$, $C(R^6R^7)OH$, or $CONHSO_2R^8$;
X is $CH_2$, O, or S;
Y is O or S;
m is 1 to 4;
n is 0 or 1; and
p is 0 or 1; or a pharmaceutically acceptable salt thereof.

A preferred embodiment of the invention is a compound of Formula Ia:

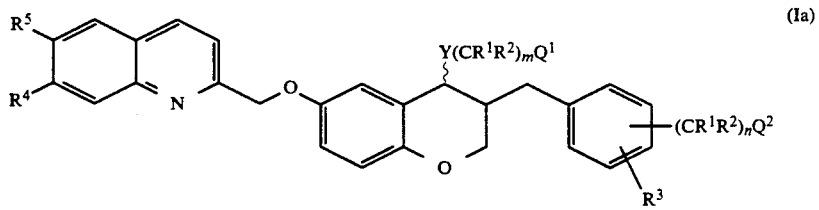

wherein the definitions are as in Formula I.

DEFINITIONS

The following abbreviations have the indicated meanings:
Ac = acetyl
Bz = benzyl
c-Bu = cyclobutyl
c-Pen = cyclopentyl
c-Pr = cyclopropyl
c-Hex = cyclohexyl
i-Pr = isopropyl
n-Pr = normal propyl
n-Bu = normal butyl
i-Bu = isobutyl
s-Bu = secondary butyl
t-Bu = tertiary butyl
DMF = N,N-dimethylformamide
DMSO = dimethyl sulfoxide
Et = ethyl
$Et_3N$ = triethylamine
Fur = furandiyl
LDA = lithium diisopropylamide
Me = methyl
Ms = methanesulfonyl = mesyl
NSAID = non-steroidal anti-inflammatory drug
Ph = phenyl
Phe = benzenediyl
Pye = pyridinediyl
r.t. = room temperature
rac. = racemic
Tf = trifluoromethanesulfonyl = triflyl
Th = 2- or 3-thienyl
THF = tetrahydrofuran
Thi = thiophenediyl
Ts = p-toluenesulfonyl = tosyl
Tz = 1H (or 2H)-tetrazol-5-yl
$C_3H_5$ = allyl The terms alkyl, alkenyl, and alkynyl mean linear and branched structures and combinations thereof.

The term "alkyl" includes "lower alkyl" and extends to cover carbon fragments having up to 20 carbon atoms. Examples of alkyl groups include octyl, nonyl, undecyl, dodecyl, tridecyl, tetradecyl, pentadecyl, eicosyl, 3,7-diethyl-2,2-dimethyl-4-propylnonyl, and the like.

The term "lower alkyl" means alkyl groups of from 1 to 7 carbon atoms. Examples of lower alkyl groups include methyl, ethyl, propyl, isopropyl, butyl, s- and t-butyl, pentyl, hexyl, heptyl, and the like.

The term "lower alkoxy" means alkoxy groups of from 1 to 7 carbon atoms of a straight, branched, or cyclic configuration. Examples of lower alkoxy groups include methoxy, ethoxy, propoxy, isopropoxy, cyclopropyloxy, cyclohexyloxy, and the like.

Substituted phenyl means a phenyl moiety with 1 or 2 substitutents selected from lower alkyl, lower alkoxy, $SCF_3$, halogen, CN, and $CF_3$.

Halogen includes F, Cl, Br, and I.

It is intended that the definitions of any substituent (e.g., $R^1$, $R^2$, etc.) in a particular molecule be independent of its definitions elsewhere in the molecule. Thus, $CR^1R^2$ represents $CH_2$, $CH(CH_3)$, $C(Et)_2$, etc.

OPTICAL ISOMERS—DIASTEREOMERS—GEOMETRIC ISOMERS

Some of the compounds described herein contain one or more asymmetric centers and may thus give rise to diastereomers and optical isomers. The present invention is meant to comprehend such possible diastereomers as well as their racemic and resolved, enantiomerically pure forms, and pharmaceutically acceptable salts thereof.

SALTS

The pharmaceutical compositions of the present invention comprise a compound of Formula I as an active ingredient or a pharmaceutically acceptable salt, thereof, and may also contain a pharmaceutically acceptable carrier and optionally other therapeutic ingredients. The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylthethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

It will be understood that in the discussion of methods of treatment which follows, references to the compounds of Formula I are meant to also include the pharmaceutically acceptable salts.

UTILITIES

The ability of the compounds of Formula I to antagonize the actions of the leukotrienes makes them useful for preventing or reversing the symptoms induced by the leukotrienes in a human subject. This antagonism of the actions of leukotrienes indicates that the compounds and pharmaceutical compositions thereof are useful to treat, prevent, or ameliorate in mammals and especially in humans: 1) pulmonary disorders including diseases such as asthma, chronic bronchitis, and related obstructive airway diseases, 2) allergies and allergic reactions such as allergic rhinitis, contact dermatitis, allergic conjunctivitis, and the like, 3) inflammation such as arthritis or inflammatory bowel disease, 4) pain, 5) skin disorders such as psoriasis, atopic eczema, and the like, 6) cardiovascular disorders such as angina, myocardial ischemia, hypertension, platelet aggregation and the like, 7) renal insufficiency arising from ischaemia induced by immunoligical or chemical (cyclosporin) etiology, 8) migraine or cluster headache, 9) ocular conditions such as uveitis, 10) hepatitis resulting from chemical, immunological or infectious stimuli, 11) trauma or shock states such as burn injuries, endotoxemia and the like, 12) allograft rejection, 13) prevention of side effects associated with therapeutic administration of cytokines such as Interleukin II and tumor necrosis factor, 14) chronic lung diseases such as cystic fibrosis, bronchitis and other small- and large-airway diseases, and 15) cholecystitis.

Thus, the compounds of the present invention may also be used to treat or prevent mammalian (especially, human) disease states such as erosive gastritis; erosive esophagitis; diarrhea; cerebral spasm; premature labor; spontaneous abortion; dysmenorrhea; ischemia; noxious agent-induced damage or necrosis of hepatic, pancreatic, renal, or myocardial tissue; liver parenchymal damage caused by hepatoxic agents such as $CCl_4$ and D-galactosamine; ischemic renal failure; disease-induced hepatic damage; bile salt induced pancreatic or gastric damage; trauma- or stress-induced cell damage; and glycerol-induced renal failure. The compounds also exhibit cytoprotective action.

The cytoprotective activity of a compound may be observed in both animals and man by noting the increased resistance of the gastrointestinal mucosa to the noxious effects of strong irritants, for example, the ulcerogenic effects of aspirin or indomethacin. In addition to lessening the effect of non-steroidal anti-inflammatory drugs on the gastrointestinal tract, animal studies show that cytoprotective compounds will prevent gastric lesions induced by oral administration of strong acids, strong bases, ethanol, hypertonic saline solutions, and the like.

Two assays can be used to measure cytoprotective ability. These assays are; (A) an ethanol-induced lesion assay and (B) an indomethacin-induced ulcer assay and are described in EP 140,684.

DOSE RANGES

The magnitude of prophylactic or therapeutic dose of a compound of Formula I will, of course, vary with the nature of the severity of the condition to be treated and with the particular compound of Formula I and its route of administration. It will also vary according to the age, weight and response of the individual patient. In general, the daily dose range for anti-asthmatic, anti-allergic or anti-inflammatory use and generally, uses other than cytoprotection, lie within the range of from about 0.001 mg to about 100 mg per kg body weight of a mammal, preferably 0.01 mg to about 10 mg per kg, and most preferably 0.1 to 1 mg per kg, in single or divided doses. On the other hand, it may be necessary to use dosages outside these limits in some cases.

For use where a composition for intravenous administration is employed, a suitable dosage range for anti-asthmatic, anti-inflammatory, or anti-allergic use is from about 0.001 mg to about 25 mg (preferably from 0.01 mg to about 1 mg) of a compound of Formula I per kg of body weight per day and for cytoprotective use from about 0.1 mg to about 100 mg (preferably from about 1 mg to about 100 mg and more preferably from about 1 mg to about 10 mg) of a compound of Formula I per kg of body weight per day.

In the case where an oral composition is employed, a suitable dosage range for anti-asthmatic, anti-inflammatory or anti-allergic use is, e.g. from about 0.01 mg to about 100 mg of a compound of Formula I per kg of body weight per day, preferably from about 0.1 mg to about 10 mg per kg and for cytoprotective use from 0.1 mg to about 100 mg (preferably from about 1 mg to about 100 mg and more preferably from about 10 mg to about 100 mg) of a compound of Formula I per kg of body weight per day.

For the treatment of diseases of the eye, ophthalmic preparations for ocular administration comprising 0.001–1% by weight solutions or suspensions of the compounds of Formula I in an acceptable ophthalmic formulation may be used.

The exact amount of a compound of the Formula I to be used as a cytoprotective agent will depend on, inter alia, whether it is being administered to heal damaged cells or to avoid future damage, on the nature of the damaged cells (e.g., gastrointestinal ulcerations vs. nephrotic necrosis), and on the nature of the causative agent. An example of the use of a compound of the Formula I in avoiding future damage would be co-administration of a compound of the Formula I with an NSAID that might otherwise cause such damage (for example, indomethacin). For such use, the compound of Formula I is administered from 30 minutes prior up to 30 minutes after administration of the NSAID. Preferably it is administered prior to or simultaneously with the NSAID, (for example, in a combination dosage form).

PHARAMACEUTICAL COMPOSITIONS

Any suitable route of administration may be employed for providing a mammal, especially a human with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like.

The pharmaceutical compositions of the present invention comprise a compound of Formula I as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently present in unit dosage form and prepared by any of the methods well-known in the art of pharmacy.

For administration by inhalation, the compounds of the present invention are conveniently delivered in the form of an aerosol spray presentation from pressurized packs of nebulisers. The compounds may also be delivered as powders which may be formulated and the powder composition may be inhaled with the aid of an insufflation powder inhaler device. The preferred delivery system for inhalation is a metered dose inhalation (MDI) aersol, which may be formulated as a suspension or solution of a compound of Formula I in suitable propellants, such as fluorocarbons or hydrocarbons.

Suitable topical formulations of compounds of formula I include transdermal device, aerosols, creams, ointments, lotions, dusting powders, and the like.

In practical use, the compounds of Formula I can be combined as the active ingredient in intimate admixture with a pharmaceutical carrier according to conventional pharmaceutical compound techniques. The carrier may take a wide variety of forms depending on the form of preparation desired for administration, e.g., oral or parenteral (including intravenous). In preparing the compositions for oral dosage form, any of the usual pharmaceutical media may be employed, such as, for exampel, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, capsules and tablets, with the solid oral preparations being preferred over the liquid preparations. Because of their ease of administration, tablets and capsules represent the most advantageous oral doage unit form in which case solid pharmaceutical carriers are obviously employed. If desired, tablets may be coated by standard aqueous or nonaqueous techniques.

In addition to the common dosage forms set out above, the compounds of Formula I may also be administered by controlled release means and/or delivery devices such as those described in U.S. Pat. 3,845,770; 3,916,899; 3,536,809; 3,598,123; 3,630,200 and 4,008,719; the disclosures of which are hereby incorporated herein by reference.

Pharmaceutical compositions of the present invention suitable for oral adminstration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divide solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optioanlly mixed with a binder, lubricant, inert diluent, surface active or dispersing agent. Molded tablets may be made by molding in a suitable machine, a mixture of the powdered compound moistened with an inert liquid diluent. Desirably, each tablet contains from about 2.5 mg to about 500 mg of the active ingredient and each cachet or capsule contains from about 2.5 to about 500 mg of the active ingredient.

The following are examples of representative pharmaceutical dosage forms for the compounds of Formula I:

| Injectable Suspension (I.M.) | mg/ml |
| --- | --- |
| Compound of Formula I | 10 |
| Methylcellulose | 5.0 |
| Tween 80 | 0.5 |
| Benzyl alcohol | 9.0 |
| Benzalkonium chloride | 1.0 |
| Water for injection to a total volume of 1 ml | |

| Tablet | mg/tablet |
| --- | --- |
| Compound of Formula I | 25 |
| Microcrystalline Cellulose | 415 |
| Providone | 14.0 |
| Pregelatinized Starch | 43.5 |
| Magnesium Stearate | 2.5 |
| | 500 |

| Capsule | mg/capsule |
| --- | --- |
| Compound of Formula I | 25 |
| Lactose Powder | 573.5 |
| Magnesium Stearate | 1.5 |
| | 600 |

| Aerosol | Per canister |
| --- | --- |
| Compound of Formula I | 24 mg |
| Lecithin, NF Liquid Concentrate | 1.2 mg |
| Trichlorofluoromethane, NF | 4.025 gm |
| Dichlorodifluoromethane, NF | 12.15 gm |

COMBINATIONS WITH OTHER DRUGS

In addition to the compounds of Formula I, the pharmaceutical compositions of the present invention can also contain other active ingredients, such as cyclooxygenase inhibitors, non-steroidal anti-inflammatory drugs (NSAIDs), peripheral analgesic agents such as zomepirac diflunisal, and the like. The weight ratio of the compound of the Formula I to the second active ingredient may be varied and will depend upon the effective dose of each ingredient. Generally, an effective dose of each will be used. Thus, for example, when a compound of the Formula I is combined with an NSAID the weight ratio of the compound of the Formula I to the NSAID will generally range from about 1000:1 to about 1:100, preferably about 200:1 to about 1:200. Combinations of a compound of the Formula I and other active ingredients will generally also be within the aforementioned range, but in each case, an effective dose of each active ingredient should be used. NSAIDS can be characterized into five groups:

(1) proprionic acid derivatives;
(2) acetic acid derivatives;
(3) fenamic acid derivatives;
(4) oxicams; and
(5) biphenylcarboxylic acid derivatives, or a pharmaceutically acceptable salt thereof.

The propionic acid derivatives which may be used comprise: aliminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, prano-profen, suprofen, tiaprofenic acid, and tioxaprofen. Structurally related propionic acid derivatives having similar analgesic and anti-inflammatory properties are also intended to be included in this group.

Thus, "propionic acid derivatives" as defiend herein are non-marcotic analgesics/non-steroidal anti-inflammatory drugs having a free $-CH(CH_3)COOH$ or $-CH_2CH_2COOH$ group (which optionally can be in the form of a pharmaceutically acceptable salt group, e.g., $-CH(CH_3)COO^-Na^+$ or $-H_2CH_2COO^-Na^+$), typically attached directly or via a carbonyl function to a ring system, preferably to an atomatic ring system.

The acetic acid derivatives which may be used comprise: indomethacin, which is a preferred NSAID, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac. Structurally related acetic acid derivatives having similar analgesic and anti-inflammatory properties are also intended to be encompassed by this group.

Thus, "acetic acid derivatives" as defined herein are non-narcotic analgesics/non-steroidal anti-inflammatory drugs having a free $-CH_2COOH$ group (which optionally can be in the form of a pharmaceutically acceptable salt group, e.g. $-CH_2COO^-Na^+$), typically attached directly to a ring system, preferably to an aromatic or heteroaromatic ring system.

The fenamic acid derivatives which may be used comprise: flufenamic acid, meclofenamic acid, mefenamic acid, niflumic acid and tolfenamic acid. Structurally related fenamic acid derivatives having similar analgesic and anti-inflammory properties are also intended to be encompassed by this group.

Thus, "fenamic acid derivatives" as defined herein are non-narcotic analgesics/non-steroidal anti-inflammatory drugs which contain the basic structure:

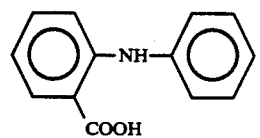

which can bear a variety of substituents and in which the free $-COOH$ group can be in the form of a pharmaceutically acceptable salt group, e.g., $-COO^{-Na+}$.

The biphenylcarboxylic acid derivatives which can be used comprise: diflunisal and flufenisal. Structurally related biphenylcarboxylic acid derivatives having similar analgesic and anti-inflammatory properties are also intended to be encompassed by this group.

Thus, "biphenylcarboxylic acid derivatives" as defined herein are non-narcotic analgesics/non-steroidal anti-inflammatory drugs which contain the basic structure:

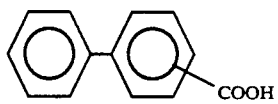

which can bear a variety of substituents and in which the free —COOH group can be in the form of a pharmaceutically acceptable salt group, e.g., —COO$^{-Na+}$.

The oxicams which can be used in the present invention comprise: isoxican, piroxicam, sudoxicam and tenoxican. Structurally related oxicams having similar analgesic and anti-inflammatory properties are also intended to be encompassed by this group.

Thus, "Oxicams" as defined herein are non-narcotic analgesics/non-steroidal anti-inflammatory drugs which have the general formula:

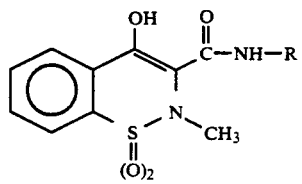

wherein R is an aryl or heteroaryl ring system.

The following NSAIDs may also be used: amfenac sodium, samainoprofen, anitrazagan, antrafenine, aurasnofin, bendazac lysinate, benzydanine, beprozine, broperamole, bufezolac, cinmetacin, ciproquazone, cloximate, dazidamine, deboxamet, demetacin, detomidine, dexindroprofen, diacerein, di-fisalamine, difenpyramide emorfazone, enfanamic acid, enolicam, epirizole, etersalate, etodolac, etofenamate, fanetizole mesylate, fenclorac, fendosal, fenflumizole, feprazone, floctafenine, flunixin, flunoxaprofen, fluproquazone, fopirtoline, fosfosal, furcloprofen, glucametacin, guaimesal, ibuproxam, isofezolac, isonixim, isoprofen, isoxicam, lefetamine HCl, leflunomide, lofemizaole, lonazolac calcium, lotifazole, loxoprofen, lysin clonixinate, meclofenamate sodium, meseclazone, nabumetone, nictindole, nimesulide, orpanoxin, oxametacin, oxapadol, perisoxal citrate, pimeprofen, pimetacin, piproxen, pirazolac, pirfenidone, proglumetacin maleate, proquazone, pyridoxiprofen, sudoxicam, talmetacin, talniflumate, tenoxicam, thiazolinobutazone, thielavin B, tiaramide HCl, tiflamizole, timegadine, tolpadol, tryptamid, and ufenamate.

The following NSAIDs, designated by company code number (see e.g., Pharmaprojects), may also be used:
480156S, AA861, AD1590, AFP802, AFP860, AI77B, AP504, AU8001, BPPC, BW540C, CHINOIN 127, CN100, EB382, EL508, F1044, GV3658, ITF182, KCNTEI6090, KME4, LA2851, MR714, MR897, MY309, PNP3144, PR823, PV102, PV108, R830, RS2131, SCR152, SH440, SIR133, SPSS510, SQ27239, ST281, SY6001, TA60, TAO-901 (4-benzxoyl-1-indancarboxylic acid), TVX2706, U60257, UR2301, and WY41770.

Finally, NSAIDs which may also be used ionclude the salicylates, specifically acetyl salicylic acid and the phenylbutazones, and pharmaceutically acceptable salts thereof.

In addition to indomethacin, other preferred NSAIDs are acetyl salicylic acid, diclofenac, fenbufen, fenoprofen, flurbiprofen, ibuprofen, ketoprofen, naproxen, phenylbutazone, piroxicam, sulindac, and tolmetin.

Pharmaceutical compositions comprising the Formula I compounds may also contain inhibitors of the biiosynthesis of the leukotrienes such as are disclosed in EP 138,481 (Apr. 24, 1985), EP 115,394 (Aug. 8, 1984), EP 136,893 (Apr. 10, 1985), and EP 140,709 (May 8, 1985), which are hereby incorporated herein by reference.

The compounds of the Formula I may also be used in combination with leukotriene antagonists such as those disclosed in EP 106,565 (Apr. 25, 1984) and EP 104,885 (Apr. 4, 1984) which are hereby incorporated herein by reference and others known in the art such as those disclosed in EP Application Nos. 56,172 (Jul. 21, 1982) and 61,800 (Jun. 10, 1982); and in U.K. Patent Spefication No. 2,058,785 (Apr. 15, 1981), which are hereby incorporated herein by reference.

Pharmaceutical compositions comprising the Formula I compounds may also contain as the second active ingredient, prostaglandin antagonists such as those disclosed in EP 11,067 (May 28, 1980) or thromboxane antagonists such as those disclosed in U.S. Pat. No. 4,237,160. They may also contain histidine decarboxylase inhibitors such as α-fluoromethylhistidine, described in U.S. Pat. No. 4,325,961. The compounds of the Formula I may also be advantageously combined with an $H_1$- or $H_2$-receptor antagonist, such as for instance acetamazole, aminothiadiazoles disclosed in EP 40,696 (Dec. 2, 1981), benadryl, cimetidine, famotidine, framamine, histadyl, phenergan, ranitidine, terfenadine and like compounds, such as those disclosed in U.S. Pat. Nos. 4,283,408; 4,362,736; and 4,394,508. The pharmaceutical compositions may also contain a $K^+/H^+ATP$ase inhibitor such as omeprazole, disclosed in U.S. Pat. No. 4,255,431, and the like. Compounds of Formula I may also be usefully combiend with most cell stabilizing agents, such as 1,3-bis(2-carboxy-chromon-5-yloxy)-2-hydroxypropane and related compounds described in British Patent Specifications 1,144,905 and 1,144,906. Another useful pharmaceutical composition comprises the Formula I compounds in combinations with serotonin antagonists such as methysergide, the serotonin antagonists described in Nature, 316, 126–131 (1985), and the like. Each of the references referred to in this paragraph is hereby incorporated herein by reference.

Other advantageous pharmaceutical compositions comprise the Formula I compounds in combination with the anti-cholinergics such as ipratropium bromide, bronchodilators such as the beta agonist salbutamol, metaproterenol, terbutaline, fenoterol and the like, and the anti-asthmatic drugs theophylline, choline theophyllinate and enprofylline, the calcium antagonists and nifedipine, diltiazem, nitrendipine, verapamil, nimodipine, felodipine, etc. and the corticosteroids, hydrocortisone, methylprednisolone, betamethasone, dexamethasone, beclomethasone, and the like.

METHODS OF SYNTHESIS

Compouds of the present invention can be prepared according to the following methods. Temperatures are in degree Celsius.

SCHEME I

Hydroxychromanone (hydroxylthiochromanone, hydroxyindaneone, hydroxybenzofuranone, or hydroxytetralone) of general structure II is protected as its benzyl ether III by refluxing the phenol II with benzyl bromide and potassium carbonate in acetone. Coupling of III with formylbenzoic acid IV using sodium hydroxide in methanol gives the enone V. The latter is hydrogenated to the corresponding saturated phenol which may be converted to the ester VI with diazomethane. Reduction of the ketone with sodium borohydride gives a mixture of diastereomeric alcohols VII. Compounds VII is coupled with a bromomethyl quinoline (VIII) by refluxing the mixture with potassium carbonate in acetone to give compound IX. Alcohol IX may be converted to XI by treatment with ester X and boron trifluoride etherate. Hydrolysis of the resulting diester gives the diacid XI. Alternatively, the ketoester VI may be coupled to VIII to give XII. Treatment of the ester XII with dimethylaluminum dimethyl amide converts the ester to the corresponding dimethylamide XIII. Reduction of the ketone of XIII with sodium borohydride gives the alcohol XIV which may be tranformed to the correspondin mesylate. Subsequent displacement of the mesylate with an alkoxide or mercaptoalkanoate (X) and hydrolysis gives compound XV. Both XI and XV are examples of compound I of the present invention.

It will be obvious to one skilled in the art that compounds VII and XIV may be resolved to the corresponding chiral stereoisomers of desired geometry. Mesylation of the chiral alcohols IX and XIV followed by displacement of the resulting mesylates with X will give the corresponding chiral products XI and XV.

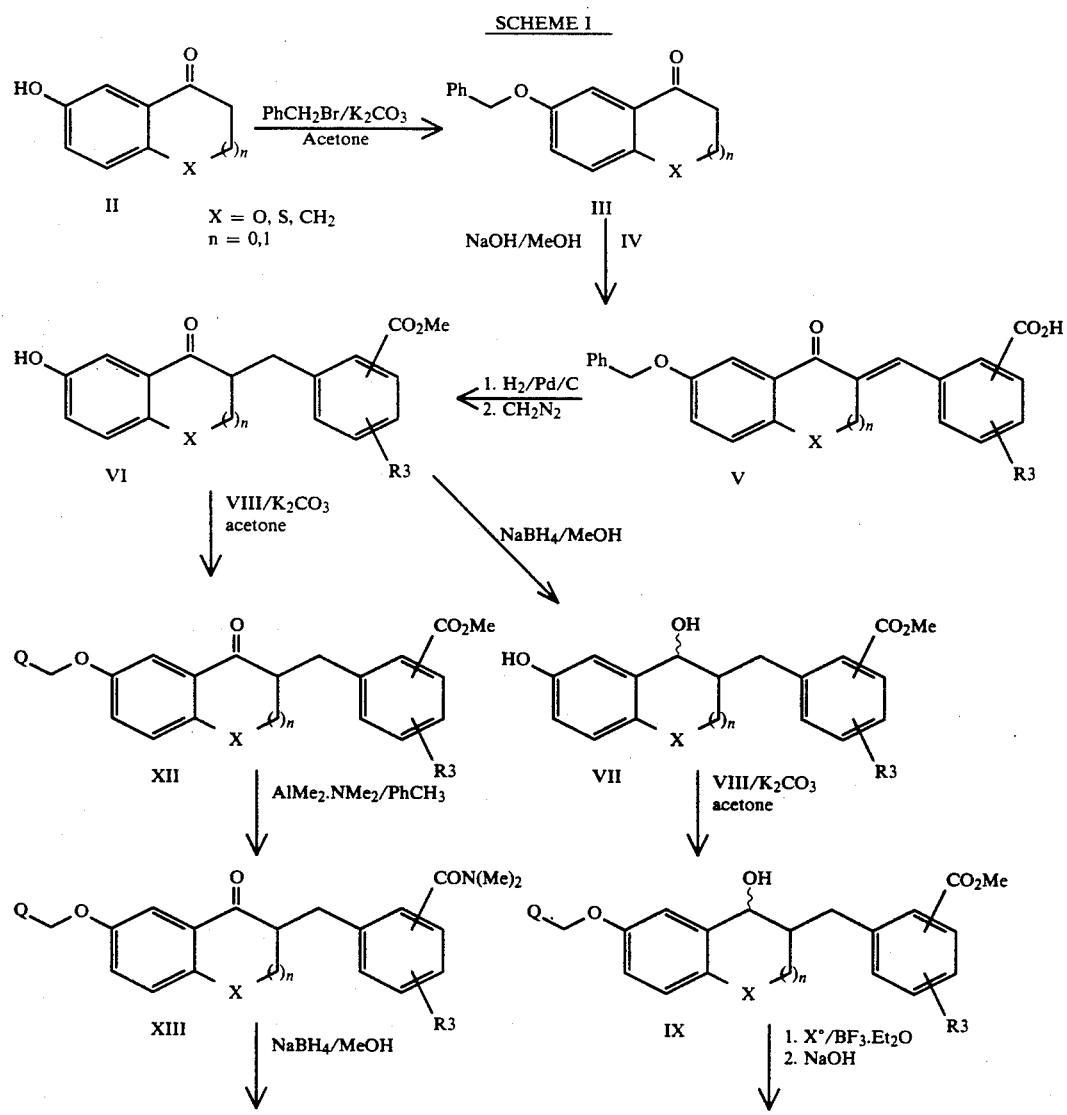

SCHEME I

-continued
SCHEME I

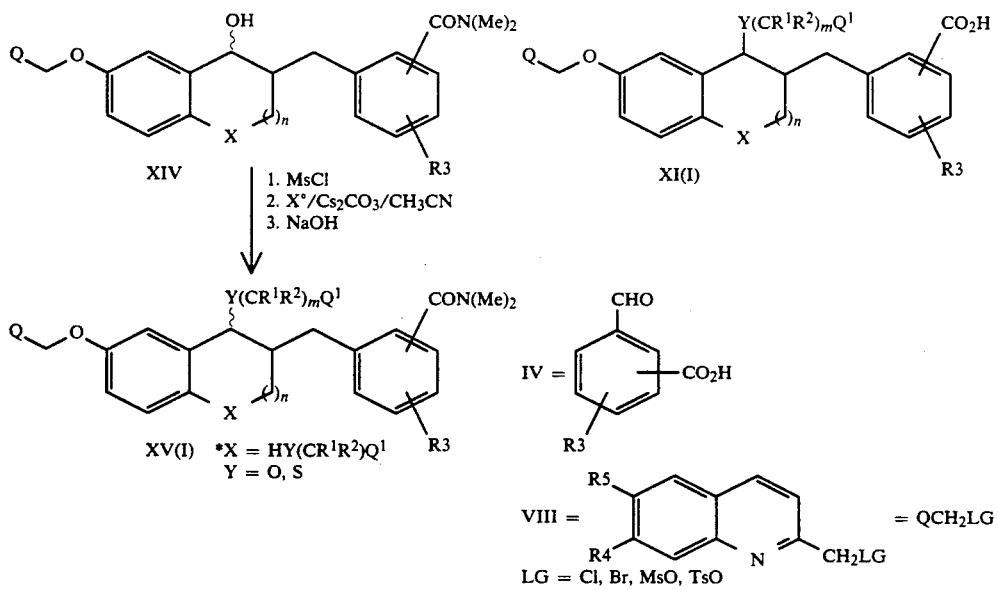

Scheme II

Other compounds of Formula I can be prepared as indicated in Scheme II. Thus, reaction of the ester XII of Scheme I with dimetylaluminum amide in refluxing xylene will give the corresponding nitrile XVI which reacts with tri-n-butyltin azide to give the corresponding tetrazole XVII. Carboxylic acid XVIII can be converted to the acid chloride which, when reacted with an alkyl amine, yields the corresponding amide XX. The acid, when coupled with an aryl or alkyl sulfonamide in the presence of dicylohexylcarbodiimide, gives the acryl sulfonamide XXI. Reaction of the ester IV of Scheme I with one molar equivalents of alkylmagnesium bromide ($R^9$=lower alkyl) gives the corresponding ketone XXII. Reaction of IX with two molar equivalents of alkylmagnesium bromine ($R^6$, $R^7$=loweralkyl) in toluene gives the corresponding tertiary alcohol XXIII. Alternatively, reaction of IX with one equivalent of $R^6$MgX followed by reduction with $NaBH_4$ yields of secondary alcohol XXIII $R^7$=H).

Compounds XVI, XVII, and XX-XXIII may then be converted to compounds of Formula I in the same way as described in Scheme I.

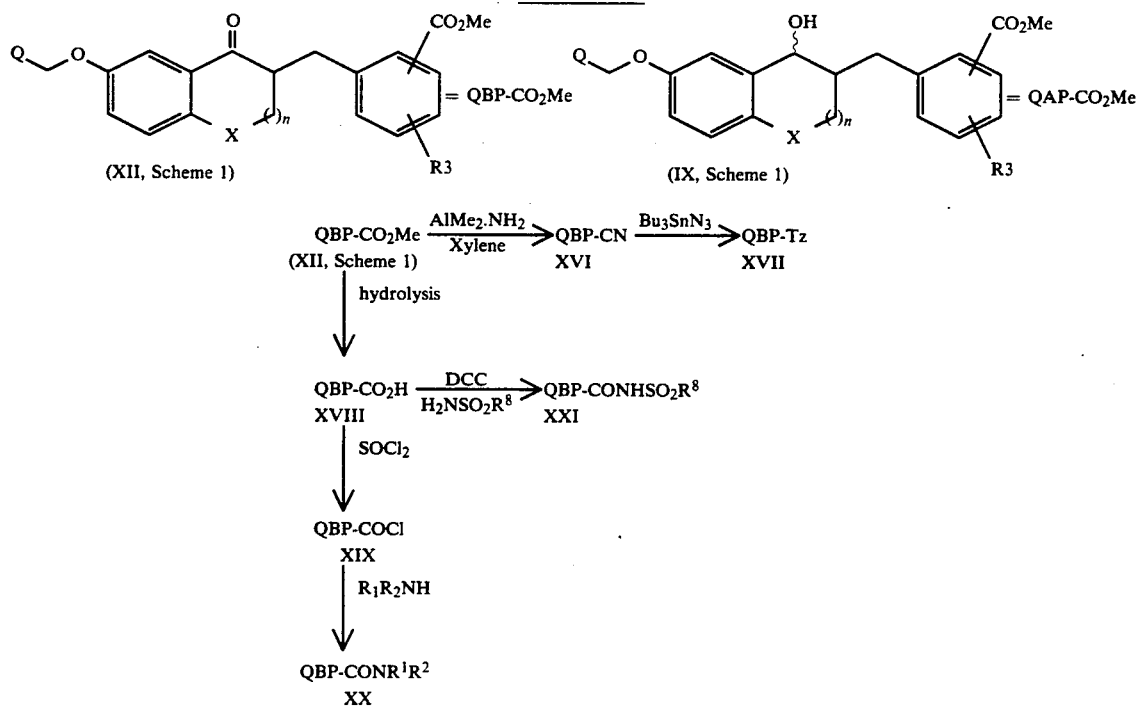

-continued
SCHEME II

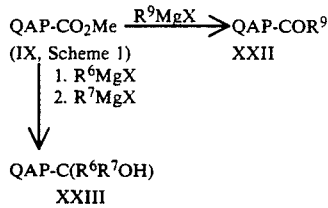

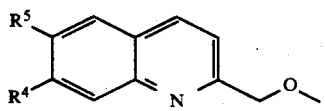

REPRESENTATIVE COMPOUNDS

Table I illustrates compounds of Formula I, which are representative of the present invention

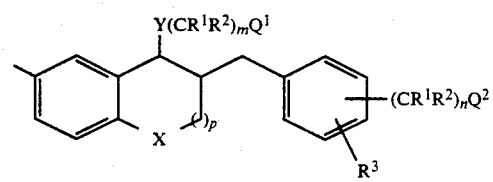

wherein the substituents are as follows:

LTD$_4$ RECEPTOR BINDING ASSAYS IN GUINEA PIG LUNG MEMBRANES AND GUINEA PIG TRACHEA AND IN VIVO ASSAYS IN ANESTHETIZED GUINEA PIGS

A complete description of these three tests is given by T. R. Jones et al., Can. J. Physiol. Pharmacol., 1989, 67, 17-28.

ASTHMATIC RAT ASSAY

Rats are obtained from an inbred line of asthmatic rats. Both female (190-250 g) and male (260-400 g) rats are used.

Egg albumin (EA), grade V, crystallized and lyophilized, is obtained from Sigma Chemical Co., St. Louis. Aluminum hydroxide is obtained from the Regis Chemical Company, Chicago. Methysergide bimaleate is supplied by Sandoz Ltd., Basel.

The challenge and subsequent respiratory recordings

TABLE I

| Ex. No. | R$^3$ | R$^4$ | R$^5$ | p | X | Y | (CR$^1$R$^2$)$_m$Q$^1$ | (CR$^1$R$^2$)$_n$Q$^2$ |
|---|---|---|---|---|---|---|---|---|
| 1 | H | Cl | H | 1 | O | S | CH$_2$CH$_2$CO$_2$H | 3-CO$_2$H |
| 2 | H | Cl | H | 0 | CH$_2$ | S | CH$_2$CH$_2$CO$_2$H | 2-CO$_2$H |
| 3a | H | Cl | H | 0 | CH$_2$ | S | CH$_2$CH$_2$CO$_2$H | CONMe$_2$ |
| 3b | H | Cl | H | 0 | CH$_2$ | S | CH$_2$CH$_2$CO$_2$H | CONMe$_2$ |
| 4 | H | Br | H | 0 | CH$_2$ | S | CH$_2$CH$_2$CO$_2$H | 4-CO$_2$H |
| 5 | H | Cl | H | 0 | CH$_2$ | S | CH$_2$CH$_2$CO$_2$H | 2-CONMe$_2$ |
| 6 | Cl | Cl | H | 0 | CH$_2$ | S | CH$_2$CH$_2$CO$_2$H | 2-CONH$_2$ |
| 7 | H | Cl | H | 1 | O | S | CH$_2$CH$_2$C(CH$_3$)CO$_2$H | 3-C(CH$_3$)$_2$OH |
| 8 | H | Cl | H | 1 | O | O | CH$_2$CH$_2$CO$_2$H | 3-CONH-t-Bu |
| 9 | H | Cl | H | 0 | CH$_2$ | S | CH$_2$CH$_2$Tz | 3-CO$_2$H |
| 10 | Cl | Cl | H | 0 | CH$_2$ | S | CH$_2$CH$_2$CO$_2$H | 3-Tz |
| 11 | H | Br | Cl | 0 | CH$_2$ | O | CH$_2$CH$_2$CO$_2$H | 3-CONMe$_2$ |
| 12 | H | Cl | H | 0 | CH$_2$ | S | CH$_2$CH$_2$Tz | 3-CONMe$_2$ |
| 13 | H | Cl | H | 1 | CH$_2$ | S | CH$_2$CH$_2$CO$_2$H | 3-CO$_2$H |
| 14 | Cl | Cl | H | 1 | CH$_2$ | S | CH$_2$CH$_2$Tz | 3-CO$_2$H |
| 15 | H | Cl | H | 1 | CH$_2$ | O | CH$_2$CH$_2$CO$_2$H | 3-COCF$_3$ |
| 16 | H | Br | Cl | 0 | O | S | CH$_2$CH$_2$CO$_2$H | 3-CHO |
| 17 | H | Cl | H | 1 | O | S | CH(CH$_3$)CH$_2$CO$_2$H | 2-COCH$_3$ |
| 18 | H | Cl | H | 1 | CH$_2$ | S | CH(CH$_3$)CH$_2$CONMe$_2$ | 3-CO$_2$H |
| 19 | H | Cl | H | 1 | S | S | CH$_2$CH(CH$_3$)CO$_2$H | 3-CO$_2$H |
| 20 | H | Br | H | 1 | S | O | CH$_2$CH(CH$_3$)CO$_2$H | 3-CO$_2$H |
| 21 | Cl | Cl | Br | 0 | O | S | CH$_2$CH(CH$_2$CH$_3$)CO$_2$H | 3-CO$_2$H |
| 22 | H | Cl | H | 0 | CH$_2$ | S | CH$_2$CH(CH$_2$CH$_3$)CO$_2$H | 3-CO$_2$H |
| 23 | H | Cl | H | 0 | S | S | CH$_2$C(CH$_3$)$_2$CO$_2$H | 2-CONHS(O)$_2$CF$_3$ |
| 24 | H | Cl | H | 1 | O | S | CH$_2$CH(CH$_3$)CO$_2$H | 3-CONHS(O)$_2$CH$_3$ |
| 25 | H | Cl | Br | 1 | O | S | CH$_2$CH$_2$C(CH$_3$)$_2$CO$_2$H | 2-CONHS(O)$_2$Ph-2-Me |
| 26 | H | Cl | H | 1 | O | S | CH$_2$CH$_2$CONHSO$_2$Ph | 2-CH$_2$OH |
| 27 | H | Cl | H | 1 | O | S | CH$_2$CH$_2$C(CH$_3$)$_2$OH | 2-CO$_2$H |
| 28 | H | Cl | H | 1 | O | S | CH$_2$C(CH$_3$)$_2$CH$_2$CO$_2$H | 2-C(CH$_3$)$_2$OH |
| 29 | H | Cl | H | 1 | O | S | CH$_2$C(CH$_3$)$_2$CH$_2$CO$_2$H | 2-CH(OH)CH$_3$ |

ASSAYS FOR DETERMINING BIOLOGICAL ACTIVITY

The leukotriene antagonist properties of the compounds of the present invention are evaluated using the following assays.

are carried out in a clear plastic box with internal dimensions 10×6×4 inches. The top of the box is removable; in use, it is held firmly in place by four clamps and an airtight seal is maintained by a soft rubber gasket. Through the center of each end of the chamber a DeVilbiss neubulizer (No. 40) is inserted via an airtight seal and each end of the box also has an outlet. A Fleisch No. 0000 pneumotachograph is inserted into one end of the box and coupled to a Grass volumetric pressure transducer (PT5-A) which is then connected to a Beckman Type R Dynograph through appropriate couplers. While aerosolizing the antigen, the outlets are open and the pneumotachograph is isolated from the chamber. The outlets are closed and the pneumotachograph and the chamber are connected during the recording of the respiratory patterns. For challenge, 2 mL of a 3% solution of antigen in saline is placed into each nebulizer and the aerosol is generated with air from a small Potter diaphragm pump operating at 10 psi and a flow of 8 liters/minute.

Rats are sensitized by injecting (subcutaneously) 1 ml of a suspension containing 1 mg EA and 200 mg aluminum hydroxide in saline. They are used between days 12 and 24 postsensitization. In order to eliminate the serotonin component of the response, rats are pretreated intravenously 5 minutes prior to aerosol challenge with 3.0 mg/kg of methysergide. Rats are then exposed to an aerosol of 3% EA in saline for exactly 1 minute, then their respiratory profiles are recorded for a further 30 minutes. The duration of continuous dyspnea is measured from the respiratory recordings.

Compounds are generally administered either orally 1-4 hours prior to challenge or intravenously 2 minutes prior to challenge. They are either dissolved in saline or 1% methocel or suspended in 1% methocel. The volume injected is 1 ml/kg (intravenously) or 10 ml/kg (orally). Prior to oral treatment rats are starved overnight. Their activity is determined in terms of their ability to decrease the duration of symptoms of dyspnea in comparison with a group of vehicle-treated controls. Usually, a compound is evaluated at a series of doses and an $ED_{50}$ is determined. This is defined as the dose (mg/kg) which would inhibit the duration of symptoms by 50%.

PULMONARY MECHANICS IN TRAINED CONSCIOUS SQUIRREL MONKEYS

The test procedure involves placing trained squirrel monkeys in chairs in aerosol exposure chambers. For control purposes, pulmonary mechanics measurements of respiratory parameters are recorded for a period of about 30 minutes to establish each monkey's normal control values for that day. For oral administration, compounds are dissolved or suspended in a 1% methocel solution (methylcellulose, 65HG, 400 cps) and given in a volume of 1 ml/kg body weight. For aerosol administration of compounds, a DeVilbiss ultrasonic nebulizer is utilized. Pretreatment periods vary from 5 minutes to 4 hours before the monkeys are challenged with aerosol doses of either leukotriene $D_4$ ($LTD_4$) or *Ascris suum* antigen.

Following challenge, each minute of data is calculated by computer as a percent change from control values for each respiratory parameter including airway resistance ($R_L$) and dynamic compliance ($C_{dyn}$). The results for each test compound are subsequently obtained for a minimum period of 60 minutes post challenge which are then compared to previously obtained historical baseline control values for that monkey. In addition, the overall values for 60 minutes post-challenge for each monkey (historical baseline values and test values) are averaged separately and are used to calculate the overall percent inhibition of $LTD_4$ or Ascaris antigen response by the test compound. For statistical analysis, paired t-test is used. (References: McFarlane, C. S. et al., Prostaglandins, 28, 173-182 (1984) and McFarlane, C. S. et al., Agents Actions, 22, 63-68 (1987).)

PREVENTION OF INDUCED BRONCHOCONSTRICTION IN ALLERGIC SHEEP

A. Rationale

Certain allergic sheep with known sensitivity to a specific antigen (*Ascaris suum*) respond to inhalation challenge with acute and late bronchial responses. The time course of both the acute and the late bronchial responses approximates the time course observed in asthmatics and the pharmacological modification of both responses is similar to that found in man. The effects of antigen in these sheep are largely observed in the large airways and are conveniently monitored as changes in lung resistance or specific lung resistance.

B. Methods

Animal Preparation: Adult sheep with a mean weight of 35 kg (range, 18 to 50 kg) are used. All animals used meet two criteria: a) they have a natural cutaneous reaction to 1:1000 or 1:10,000 dilutions of *Ascaris suum* extract (Greer Diagnostics, Leonois, NC) and b) they have previously responded to inhalation challenge with *Ascaris suum* with both an acute bronchoconstriction and a late bronchial obstruction (W. M. Abraham et al., Am. Rev. Resp. Dis., 128, 839-44 (1983)).

Measurement of Airway Mechanics: The unsedated sheep are restrained in a cart in the prone position with their heads immobilized. After topical anesthesia of the nasal passages with 2% lidocaine solution, a balloon catheter is advanced through one nostril into the lower esophagus. The animals are then intubated with a cuffed endotracheal tube through the other nostril using a flexible fiberoptic bronchoscope as a guide. Pleural pressure is estimated with the esophageal balloon catheter (filled with one ml of air), which is positioned such that inspiration produces a negative pressure deflection with clearly discernible carbiogenic oscillations. Lateral pressure in the trachea is measured with a sidehole catheter (inner dimension, 2.5 mm) advanced through and positioned distal to the tip of the nasotracheal tube. Transpulmonary pressure, the difference between tracheal pressure and pleural pressure, is measured with a differential pressure transducer (DP45; Validyne Corp., Northridge, Calif.). For the measurement of pulmonary resistance ($R_L$), the maximal end of the nasotrachel tube is connected to a pneumotachograph (Fleisch, Dyna Sciences, Blue Bell, Pa.). The signals of flow and transpulmonary pressure are recorded on an oscilloscope (Model DR-12; Electronics for Medicine, White Plains, N.Y.) which is linked to a PDP-11 Digital computer (Digital Equipment Corp., Maynard, Mass.) for one-line calculation of $R_L$ from transpulmonary pressure, respiratory volume obtained by integration and flow. Analysis of 10-15 breaths is used for the determination of $R_L$. Thoracic gas volume ($V_{tg}$) is measured in a body plethysmograph, to obtain specific pulmonary resistance ($SR_L = R_L \cdot V_{tg}$).

Aerosol Delivery Systems: Aerosols of *Ascaris suum* extract (1:20) are generated using a disposable medical-nebulizer (Raindrop®, Puritan Bennett), which produces an aerosol with a mass median aerodynamic diameter of 6.2 $\mu M$ (geometric standard deviation, 2.1) as determined by an electric size analyzer (Model 3030; Thermal Systems, St. Paul, Minn.). The output from the nebulizer is directed into a plastic t-piece, one end of which is attached to the nasotracheal tube, the other end of which is connected to the inspiratory part of a Harvard respirator. The aerosol is delivered at a tidal volume of 500 ml of a rate of 20 per minute. Thus, each sheep receives an equivalent dose of antigen in both placebo and drug trials.

Experimental Protocol: Prior to antigen challenge baseline measurements of $SR_L$ are obtained, infusion of the test compound is started 1 hr prior to challenge, the measurement of $SR_L$ repeated and then the sheep undergoes inhalation challenge with *Ascaris suum* antigen. Measurement of $SR_L$ are obtained immediately after antigen challenge and at 1, 2, 3, 4, 5, 6, 6.5, 7, 7.5, and 8 hrs after antigen challange. Placebo and drug tests are separated by at least 14 days. In a further study, sheep are given a bolus dose of the test compound followed by an infusion of the test compound for 0.5–1 hr to Ascaris challenge and for 8 hrs after Ascaris as described above.

Statistical Analysis: A Kruskai-Wallis one way ANOVA test is used to compare the acute immediate responses to antigen and the peak late response in the controls and the drug treated animals.

The invention is further defined by reference to the following examples, which are intended to be illustrative and not limiting. All temperatures are in degrees Celsius.

EXAMPLE 1

6-(7-Chloro-2-quinolinyl)methoxy-3-(3-carboxyphenyl)methyl-4-(3-carboxyl-propylthio)chroman, disodium salt

Step 1: 6-Benzyloxy-4-chromanone

A mixture of 6-hydroxy-4-chromanone (18.6 g, 113 mmol), benzyl bromide (20 g, 116 mmol), and $K_2CO_3$ (21 g, 152 mmol) in acetone (110 ml) was refluxed for 20 hrs. The mixture was cooled, diluted with EtOAc, and filtered through celite. The filtrate was concentrated to an oil, which was triturated with 10% $Et_2O$ in hexane (150 ml) to gives, after filtration and washing, 28 g (87%) of the title compound.

Step 2: 6-Benzyloxy-3-(3-carboxyphenylmethylene)-4-chromanone

A mixture of 6-benzyloxy-4-chromanone from Step 1 (5.68 g, 20 mmol), 3-carboxybenzaldehyde (30 g, 20 mmol), and 5N NaOH (10 ml, 50 mmol) in MeOH (200 ml) was stirred at r.t. for 9 days. The mixture was diluted with $H_2O$ (500 ml), acidified with HOAc to pH 5.6, filtered and air dried to give 7.95 g (98%) of the title compound.

Step 3: 3-(3-Carbomethoxyphenyl)methyl-6-hydroxy-4-chromanone

To a solution of 6-benzyloxy-3-)3-carboxyphenylmethylene)-4-chromanone from Step 2 (1.54 g, 3.8 mmol) in 40 ml THF/MeOH (1:3) was added 150 mg of 10% Pd/C. The mixture was hydrogenated at 40 psi for 20 hr. The mixture was filtered through celite. The filtrate was evaporated to dryness and redissolved in THF. The THF solution was cooled to 0° C. and diazomethane was added until no acid remained. Then HOAc was added. The mixture was evaporated to give an oil which was chromatographed on silica gel and eluted with 40% EtOAc/hexane to give 750 mg (63%) of the title compound.

Step 4: 3-(3-Carbomethoxyphenyl)methyl-4,6-dihydroxy-chroman

To a solution of the product of Step 3 (700 mg, 2.4 mmol) in 5 ml MeOH and 1 ml THF at r.t. was added $NaBH_4$ (80 mg, 2.4 mmol). The solution was stirred at r.t. for 0.5 hr. The mixture was poured into cold $NH_4Cl$ solution, extracted with HOAc, and chromatographed on silica gel (eluted with 40% EtOAc/hexane) to give 441 mg (58%) of the cis isomer and 279 mg (37%) of the trans isomer of the title compound.

Step 5: 6-(7-Chloro-2-quinolinyl)methoxy-3-(3-carbomethoxyphenyl)methyl-4-hydroxychroman a. To a solution of the trans-isomer of Step 4 (116 mg, 0.37 mmol) in DMF (4 ml) at r.t. was added NaH (17 mg, 0.4 mmol, 60% in oil). The mixture was stirred at r.t. for 0.5 hr. 2-(Bromomethyl)-7-chloroquinoline (112 mg, 0.44 mmol) was added. Reaction was completed after 1 hr and worked up by addition of $NH_4Cl$ and extraction with EtOAc. Chromatography of the concentrated extracts gave 156 mg (86%) of the title compound.

b. The procedure was repeated using the cis-isomer of Step 4.

Step 6: 6-(7-Chloro-2-quinolinyl)methoxy-3-(3-carbamethoxyphenyl)methyl-4-(3-carbomethoxy-1-thiopropyl)chroman a. To a solution of the product of Step 5a (146 mg, 0.3 mmol) in $CH_2Cl_2$ (3ml) was added methyl 3-thiopropionate (39.6 mg, 0.33 mmol) and boron trifluoride etherate (160 mg, 1.2 mmol). The mixture was stirred at r.t. for 20 hrs, poured into aq. $NH_2OAc$ (20%), and extracted with EtOAc. Chromatography of the concentrated organic extracts on silica gel (eluted with 30% EtOAc/hexane) gave 140 mg (78%) of the title compound. This product is a mixture of cis/trans isomers.

b. The procedure was repeated using the product of Step 5b and also produced a mixture of cis/trans isomers.

Step 7: 6-(7-Chloro-2-quinolinyl)methoxy-3-(3-carboxyphenyl)methyl-4-(3-carboxy-1-thiopropyl)chroman To a solution of the product of Step 6a (140 mg, 0.23 mmol) in THF (1 ml) and EtOH (2 ml) was added LiOH (1.5 mmol, 1N). The mixture was stirred at r.t. for 20 hrs, acidified with HOAc, and extracted with ETOAc. Chromatography of the crude product on silicic acid (eluted with 30% ETOAc/hexane) gave 188 mg (91%) of the title compound as an oil.

$^1$H NMR ($CD_3COCD_3$): δ 2.4–2.95 (m, 7H), 3.9–4.15 (2H, m), 4.38 (dd, 1H, J=10.8 Hz, J=2 Hz), 5.32 (s, 2H), 6.67–7.15 (m, 3H), 7.42–8.12 (m, 8H), 8.45 (d, 1H, J=9.3 Hz).

Step 8: 6-(7-Chloro-2-quinolinyl)methoxy-3-(3-carboxyphenyl)methyl-4-(3-carboxyl-propylthio)chroman, disodium salt To the acid from Step 7 (118 mg, 0.21 mmol) in ethanol was added NaOH (1N, 0.42 mmol). The solvent was evaporated and the product was dissolved in H₂O and freeze dried to yield the title compound.

Anal. Calc'd for $C_{30}H_{24}ClNNa_2O_6S \cdot 2\frac{1}{2}H_2O$: C, 55.17; H, 4.47; N, 2.14; Na, 7.04; Found: C, 55.16; H, 4.27; N, 2.13; Na, 7.59.

EXAMPLE 2

6-(7-Chloro-2-quinolinyl)methoxy-2-(2-carboxyphenyl)methyl-1-(3-carboxypropylthio)indane, disodium salt

Step 1:
2-(2-Carboxyphenyl)methylene-6-methoxy-1-indanone

To a solution of 6-methoxy-1-indanone (15 g, 93 mmol) and 2-formylbenzoic acid (14 g, 93 mmol) in MeOH (1 L) was added NaOH (47 ml, 5N). The mixture was stirred at r.t. for 20 hrs. NH₄Cl solution was added and the resulting mixture was buffered to pH 6 with HOAc. The yellow solid was filtered, washed with H₂O, and dried in air to give 25 g (92%) of the title compound.

Step 2:
2-(2-Carboxyphenyl)methyl-6-methoxy-1-indanone

A mixture of the product of Step 1 (25 g, 85 mmol) and 10% Pd/C (2.5 g) in THF/EtOH (100 ml each) was hydrogenated at 40 psi for 5 hrs. The mixture was filtered through celite and concentrated to give 25 g of the title compound, which was used as such for the next step.

Step 3:
2-(2-Carbomethoxyphenyl)methyl-6-hydroxy-1-indanone

To a solution of the product of Step 2 (25 g, 84.5 mmol) in toluene (1.2 L) at 60° C. was added AlCl₃ (45 g, 338 mmol) in portions. The mixture was stirred at 60° C. for 14 hrs. NH₄Cl solution was added and the mixture was extracted with EtOAc. The crude concentrated extract was treated with excess CH₂N₂ in Et₂O. Chromatography of the resulting product on silica gel (eluted with 30% EtOAc/hexane) gave 17.5 g (70%) of the title compound.

Step 4:
6-(7-chloro-2-quinolinyl)methoxy-2-(2-carbomethoxyphenyl)methyl-1-indanone A mixture of the product of Step 3 (17.5 g, 59 mmol), 2-bromomethyl-7-chloroquinoline (16.65 g, 65 mmol) and K₂CO₃ (8.97 g, 65 mmol) in acetone (200 ml) was refluxed for 14 hrs. The mixture was filtered and the filtrate was concentrated in vacuo. Chromatography of the resulting crude product on silica gel (eluted with 30% EtOAc/hexane) gave 21.15 g (80%) of the title compound.

Step 5:
6-(7-chloro-2-quinolinyl)methoxy-2-(2-carbomethoxyphenyl)methyl-1-hydroxyindane To a suspension of the product of Step 4 (335 mg, 0.71 mmol) in MeOH (10 mL) was added NaBH₄ (80 mg, 2 mmol). The mixture was stirred at r.t. for 20 hrs. NH₄Cl solution was added and the mixture was extracted with Et OAc. Chromatography of the concentrated extract on silica gel (eluted with 30% EtOAc/hexane) gave 248 mg (74%) of the title compound as a mixture of cis-/trans isomers.

Step 6:
6-(7-Chloro-2-quinolinyl)methoxy-2-(2-carboxyphenyl)methyl-1-(3-carbomethoxypropylthio)indane To a solution of the product of Step 5 (200 mg, 0.42 mmol) and methyl 3-mercaptopropionate (100 mg, 0.82 mmol) in CH₂Cl₂ (15 ml) at 0° C. was added AlCl₃ (390 mg, 3 mmol). The mixture was stirred at 0° C. for 10 min. NH₄Cl solution was added and the mixture was extracted with EtOAc. Chromatography of the concentrated extract on silica gel (eluted with 20% EtOAc/hexane) gave 145 mg (60%) of the title compound as a single product of undetermined stereochemistry.

Step 7:
6-(7-Chloro-2-quinolinyl)methoxy-2-(2-carboxyphenyl)methyl-1-(3-carboxypropylthio)indane To a solution of the product of Step 6 (131 mg, 0.229 mmol) in THF/MeOH (1.5 ml, 1:2) was added 1M K₂CO₃ (0.687 ml). The mixture was stirred at room temperature for 20 hrs. NH₄Cl solution was added and the pH was adjusted to 5 with HOAc. Extraction with EtOAc followed by chromatography of the crude product on silicic acid (eluted with 30% EtOAc/hexane) gave 100 mg of the title compounds.

Step 8:
6-(7-Chloro-2-quinolinyl)methoxy-2-(2-carboxyphenyl)methyl-1-3-carboxypropylthio)indane, disodium salt To the acid from Step 7 (90 mg, 0.16 mmol) in EtOH (1 ml) was added 1N NaOH (0.32 ml). The solvent was evaporated, the residue was dissolved in water, and the solution freeze dried to yield the title compound:

¹H NMR (250 MHz, CD₃SOCD₃) δ: 2.24 (m, 2H), 2.39-3.12 (m, 3H), 3.84 (d, 1H, J=8.34 Hz), 5.21 (s, 2H), 6.72 (m, 1H), 6.93 (m, 1H), 6.97-7.16 (m, 4H), 7.3 (d, 1H, J=8.34 Hz), 7.45 (d, 1H, J=8.34 Hz), 7.63 (d, 1H, J=8.34 Hz), 7.84 (d, 1H, J=8.34 Hz), 7.92 (s, 1H), 8.26 (d, 1H, J=8.34 Hz).

Exact mass calc'd for $C_{30}H_{24}O_5NSClNa_2+H^+$: 592.09369, Found: 592.0937.

EXAMPLE 3

6-(7-Chloro-2-quinolinyl)methoxy-1-(3-carboxypropylthio)-2-(2-dimethylcarboxamidophenyl)methylindane, sodium salt

Step 1:
6-(7-Chloro-2-quinolinyl)methoxy-2-(2-dimethylcarboxamidophenyl)methyl-1-indanone To a suspension of 6-(7-chloro-2-quinolinyl)methoxy-2-(2-carbomethoxyphenyl)methyl-1-indanone (Example 2, Step 4) (2.5 g, 5.31 mmol) in toluene (15 ml) was added a solution of dimethylamino dimethyaluminum (10.62 ml, 1M) at r.t. The mixture was then stirred at 60° C. for 2 hrs. Upon cooling, HCl (1N) was added and the mixture was stirred for ½ hr before extraction with EtOAc. Chromatography of the concentrated extract on silica gel (eluted with 30% EtOAc/hexane) gave 2.6 g (100%) of the title compound.

Step 2:
6-(7-Chloro-2-quinolinyl)methoxy-2-(2-dimethylcarboxamidophenyl)methyl-1-hydroxy-indane To a suspension of the product of Step 1 (1.5 g, 3 mmol) in MeOH (45 ml) at r.t. was added NaBH₄ (1.17 g, 30 mmol). The mixture was stirred for 20 hrs. NH₄Cl solution was added and the mixture was extracted with EtOAc. Chromatography of the concentrated extract on silica gel (eluted with 30% EtOAc/hexane) gave 1.3 g (86%) of the title compound as a mixture of cis/trans isomers.

Step 3:
6-(7-Chloro-2-quinolinyl)methoxy-1-(3-carbomethoxypropylthio)-2-(2-dimethylcarboxamidophenyl)methylindane To a solution in $CH_2Cl_2$ of the product of Step 2 (128 mg, 0.263 mmol) and methyl 3-mercaptopropionate (94 mg, 0.79 mmol) at 0° C. was added $AlCl_3$ (244 mg, 1.8 mmol). The mixture was stirred at 0° C. for 10 min. $NH_4Cl$ solution (10%) was added and the mixture was extracted with EtOAc. Chromatography of the concentrated extract on silica gel (eluted with 30% EtOAc/hexane) gave 60 mg of isomer 1 and 30 mg of isomer 2 of the title compound. These are a cis/trans pair of isomers of unassigned stereochemistry.

Step 4:
6-(7-Chloro-2-quinolinyl)methoxy-2-(3-carboxy propylthio)-2-(2-dimethylcarboxamidophenyl)methylindane To a solution of each of the isomers of the product of Step 3 in THF/MeOH (1.5 ml, 1:2) was added 1N LiOH (0.5 ml). The mixture was stirred at r.t. for 5 hrs. $NH_4Cl$ solution was added and the pH was adjusted to 5 with HOAc. Extraction with EtOAc followed by chromatography of the crude products on silicic acid (eluted with 30% EtOAc/hexane) gave 50 mg of isomer 1 and 25 mg of isomer 2 of the title compounds.

Step 5:
6-(7-Chloro-2-quinolinyl)methoxy-1-(3-carboxypropylthio)-2-(2-dimethylcarboxamidophenyl)methylindane, sodium salt To each of the isomeric acids of Step 4 in EtOH (1 ml) was added 1N NaOH (0.18 ml and 0.043 ml, respectively). The solvent was evaporated and the products were dissolved in water and freeze dried to yield the title compounds.

Isomer 1

$^1H$ NMR (250 MHz, $CD_3SOCD_3$) δ: 2.05 (t, 2H, J=9.37 Hz), 2.7 (s, 3H), 2.75-2.9 (m, 3H), 2.95 (s, 3H), 3.92 (d, 1H, J=3 Hz), 5.4 (s, 2H), 6.88 (d, 1H, J=3 Hz), 5.4 (s, 2H), 6.88 (d, 1H, J=3 Hz), 7.05 (d,d, 1H, J=9.37 Hz, J'=3 Hz), 7.15 (m, 3H), 7.3 (d, 2H, J=12.5 Hz), 7.65 (d,d, 1H, J=9.37 Hz, J'=3 Hz), 7.72 (d, 1H, J=12.5 Hz), 8.05 (d, 1H, J=9.37 Hz), 8.08 (s, 1H), 8.5 (d, 1H, J=12.5 Hz).

Exact mass calc'd for $C_{32}H_{30}N_2SiO_4ClNa+H^+$: 597.1590. Found: 597.1590.

Isomer 2

$^1H$ NMR (250 MHz, $CD_3SOCD_3$), δ: 2.1 (m, 2H), 2.72 (s, 3H), 2.75-2.9 (m, 3H), 2.95 (s, 3H), 3.88 (d, 1H, J=3 Hz), 5.35 (s, 2H), 6.85 (m, 1H), 7.0 (s, 1H), 7.05 (d, 1H, J=9.37 Hz), 7.15 (m, 1H), 7.2-7.35 (m, 3H), 7.65 (d,d, 1H, J=6.25, J'=3 Hz), 7.7 (d, 1H, J=9.37 Hz), 8.08 (m, 2H), 8.45 (d, 1H, J=9.37 Hz)

What is claimed is:

1. A compound of the formula:

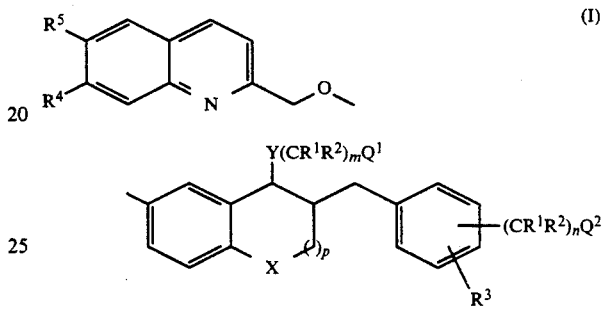

wherein:
each of $R^1$ and $R^2$ is independently H or lower alkyl;
$R^3$ is H or Cl
$R^4$ is Cl or Br;
$R^5$ is H, Cl or Br;
each of $R^6$ and $R^7$ is independently H or Lower alkyl;
$R^8$ is alkyl, substituted or unsubstituted phenyl, or $CF_3$;
$R^9$ is H, lower alkyl, or $CF_3$;
each of $Q^1$ and $Q^2$ is independently $CO_2H$, $CONR^1R^2$, 1H- (or 2H-)tetrazol-5-yl, $COR^9$, $C(R^6R^7)OH$, or $CONHSO_2R^8$;
X is $CH_2$, O, or S;
Y is O or S;
m is 1 to 4;
n is 0 or 1; and
p is 0 or 1;
or a pharmaceutically acceptable salt thereof.

2. A compound of claim 1 of the Formula Ia

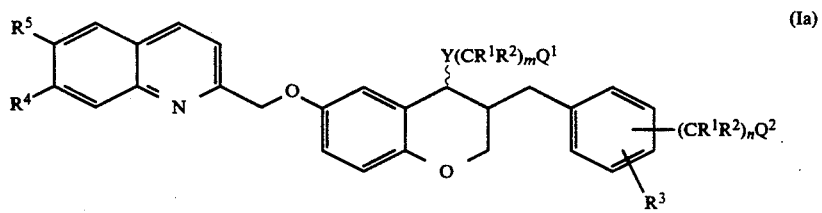

3. A compound of claim 1 wherein the substituents are as follows:

| Ex. No. | $R^3$ | $R^4$ | $R^5$ | p | X | Y | $(CR^1R^2)_mQ^1$ | $(CR^1R^2)_nQ^2$ |
|---|---|---|---|---|---|---|---|---|
| 1 | H | Cl | H | 1 | O | S | $CH_2CH_2CO_2H$ | 3-$CO_2H$ |
| 2 | H | Cl | H | 0 | $CH_2$ | S | $CH_2CH_2CO_2H$ | 2-$CO_2H$ |
| 3a | H | Cl | H | 0 | $CH_2$ | S | $CH_2CH_2CO_2H$ | $CONMe_2$ |
| 3b | H | Cl | H | 0 | $CH_2$ | S | $CH_2CH_2CO_2H$ | $CONMe_2$ |
| 4 | H | Br | H | 0 | $CH_2$ | S | $CH_2CH_2CO_2H$ | 4-$CO_2H$ |
| 5 | H | Cl | H | 0 | $CH_2$ | S | $CH_2CH_2CO_2H$ | 2-$CONMe_2$ |

-continued

| Ex. No. | $R^3$ | $R^4$ | $R^5$ | p | X | Y | $(CR^1R^2)_mQ^1$ | $(CR^1R^2)_nQ^2$ |
|---|---|---|---|---|---|---|---|---|
| 6 | Cl | Cl | H | 0 | $CH_2$ | S | $CH_2CH_2CO_2H$ | 2-$CONH_2$ |
| 7 | H | Cl | H | 1 | O | S | $CH_2CH_2C(CH_3)CO_2H$ | 3-$C(CH_3)_2OH$ |
| 8 | H | Cl | H | 1 | O | O | $CH_2CH_2CO_2H$ | 3-CONH-t-Bu |
| 9 | H | Cl | H | 0 | $CH_2$ | S | $CH_2CH_2Tz$ | 3-$CO_2H$ |
| 10 | Cl | Cl | H | 0 | $CH_2$ | S | $CH_2CH_2CO_2H$ | 3-Tz |
| 11 | H | Br | Cl | 0 | $CH_2$ | O | $CH_2CH_2CO_2H$ | 3-$CONMe_2$ |
| 12 | H | Cl | H | 0 | $CH_2$ | S | $CH_2CH_2Tz$ | 3-$CONMe_2$ |
| 13 | H | Cl | H | 1 | $CH_2$ | S | $CH_2CH_2CO_2H$ | 3-$CO_2H$ |
| 14 | Cl | Cl | H | 1 | $CH_2$ | S | $CH_2CH_2Tz$ | 3-$CO_2H$ |
| 15 | H | Cl | H | 1 | $CH_2$ | O | $CH_2CH_2CO_2H$ | 3-$COCF_3$ |
| 16 | H | Br | Cl | 0 | O | S | $CH_2CH_2CO_2H$ | 3-CHO |
| 17 | H | Cl | H | 1 | O | S | $CH(CH_3)CH_2CO_2H$ | 2-$COCH_3$ |
| 18 | H | Cl | H | 1 | $CH_2$ | S | $CH(CH_3)CH_2CONMe_2$ | 3-$CO_2H$ |
| 19 | H | Cl | H | 1 | S | S | $CH_2CH(CH_3)CO_2H$ | 3-$CO_2H$ |
| 20 | H | Br | H | 1 | S | O | $CH_2CH(CH_3)CO_2H$ | 3-$CO_2H$ |
| 21 | Cl | Cl | Br | 0 | O | S | $CH_2CH(CH_2CH_3)CO_2H$ | 3-$CO_2H$ |
| 22 | H | Cl | H | 0 | $CH_2$ | S | $CH_2CH(CH_2CH_3)CO_2H$ | 3-$CO_2H$ |
| 23 | H | Cl | H | 0 | S | S | $CH_2C(CH_3)_2CO_2H$ | 2-$CONHS(O)_2CF_3$ |
| 24 | H | Cl | H | 1 | O | S | $CH_2CH(CH_3)CO_2H$ | 3-$CONHS(O)_2CH_3$ |
| 25 | H | Cl | Br | 1 | O | S | $CH_2CH_2C(CH_3)_2CO_2H$ | 2-$CONHS(O)_2Ph$-2-Me |
| 26 | H | Cl | H | 1 | O | S | $CH_2CH_2CONHSO_2Ph$ | 2-$CH_2OH$ |
| 27 | H | Cl | H | 1 | O | S | $CH_2CH_2C(CH_3)_2OH$ | 2-$CO_2H$ |
| 28 | H | Cl | H | 1 | O | S | $CH_2C(CH_3)_2CH_2CO_2H$ | 2-$C(CH_3)_2OH$ |
| 29 | H | Cl | H | 1 | O | S | $CH_2C(CH_3)_2CH_2CO_2H$ | 2-$CH(OH)CH_3$ |

4. A pharmaceutical composition comprising a compound of claim 1 and a pharmaceutically acceptable carrier.

* * * * *